(12) United States Patent
Tsugita et al.

(10) Patent No.: US 6,315,787 B1
(45) Date of Patent: *Nov. 13, 2001

(54) SUTURELESS VESSEL PLUG AND METHODS OF USE

(75) Inventors: Ross S. Tsugita, Mountain View; Richard Lilly, San Jose, both of CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,799

(22) Filed: May 2, 2000

Related U.S. Application Data

(63) Continuation of application No. 09/199,233, filed on Nov. 24, 1998, now Pat. No. 6,080,183.

(51) Int. Cl.⁷ .................................................. A61B 17/08
(52) U.S. Cl. ............................................................ 606/213
(58) Field of Search ................................. 606/213, 151, 606/75, 232, 72, 73, 144, 148

(56) References Cited

U.S. PATENT DOCUMENTS

| | | | |
|---|---|---|---|
| 4,895,148 | 1/1990 | Bays et al. | 606/213 |
| 5,009,643 | 4/1991 | Reich et al. | 604/165 |
| 5,032,125 * | 7/1991 | Durham et al. | 606/62 |
| 5,403,329 | 4/1995 | Hinchcliffe | 606/147 |
| 5,417,699 | 5/1995 | Klein et al. | 606/144 |
| 5,425,757 * | 6/1995 | Tiefenbrun et al. | 623/2 |
| 5,470,338 | 11/1995 | Whitfield et al. | 606/144 |
| 5,474,568 | 12/1995 | Scott | 606/144 |
| 5,478,344 | 12/1995 | Stone et al. | 606/144 |
| 5,480,403 | 1/1996 | Lee et al. | 606/72 |
| 5,527,322 | 6/1996 | Klein et al. | 606/144 |
| 5,540,675 | 7/1996 | Hasson | 606/1 |
| 5,562,689 | 10/1996 | Green et al. | 606/151 |
| 5,568,746 | 10/1996 | Culligan et al. | |
| 5,569,301 | 10/1996 | Granger et al. | 606/224 |
| 5,586,986 | 12/1996 | Hinchcliffe | 606/147 |
| 5,591,180 | 1/1997 | Hinchcliffe | 606/144 |
| 5,591,181 | 1/1997 | Stone et al. | 606/144 |
| 5,613,974 | 3/1997 | Andreas et al. | 606/144 |
| 5,645,552 | 7/1997 | Sherts | 606/145 |
| 5,645,565 | 7/1997 | Rudd et al. | 606/213 |
| 5,662,663 | 9/1997 | Shallman | 606/144 |
| 5,728,113 | 3/1998 | Sherts | 606/145 |
| 5,741,282 * | 4/1998 | Anspach, III et al. | 606/151 |
| 5,746,755 | 5/1998 | Wood et al. | 606/148 |
| 5,779,719 | 7/1998 | Klein et al. | 606/144 |
| 5,792,152 | 8/1998 | Klein et al. | 606/144 |
| 5,860,991 | 1/1999 | Klein et al. | 606/144 |
| 5,902,311 | 5/1999 | Andreas et al. | 606/144 |
| 5,921,994 | 7/1999 | Andreas et al. | 606/144 |
| 5,938,668 | 8/1999 | Scirica et al. | 606/145 |
| 5,948,000 | 9/1999 | Larsen et al. | 606/232 |
| 5,948,001 | 9/1999 | Larsen | 606/232 |
| 6,056,751 * | 5/2000 | Fenton, Jr. | 606/72 |
| 6,080,183 * | 6/2000 | Tsugita et al. | 606/213 |

\* cited by examiner

Primary Examiner—Olik Chaudhuri
Assistant Examiner—Vikki Hoa Trinh
(74) Attorney, Agent, or Firm—Lyon & Lyon LLP

(57) ABSTRACT

A vessel plug having a handle which include a proximal end and a distal end, a flange attached to the distal end of the handle, and a tip extending distally beyond the flange. In use, the flange and the tip are shaped to engage an opening of a blood vessel, provide occlusion to the opening of the vessel to block the blood flow, thereby achieving hemostasis. The plug may be sutureless, providing a seal by the operation of a flange that includes vacuum ports or adhesive material. Alternatively, sutures may be placed around the flange. Methods of using the sutureless vessel plug are also disclosed herein.

15 Claims, 6 Drawing Sheets

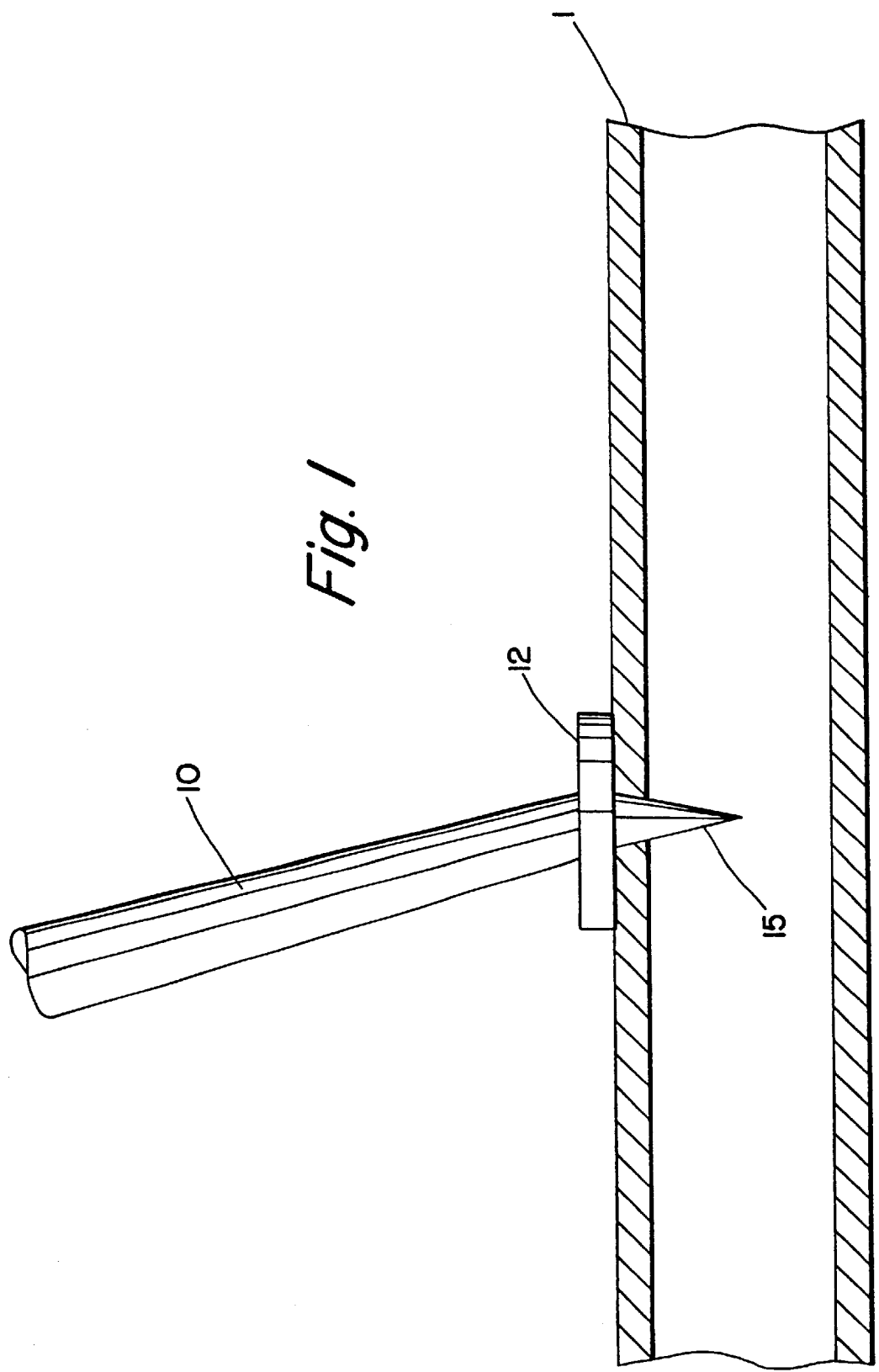

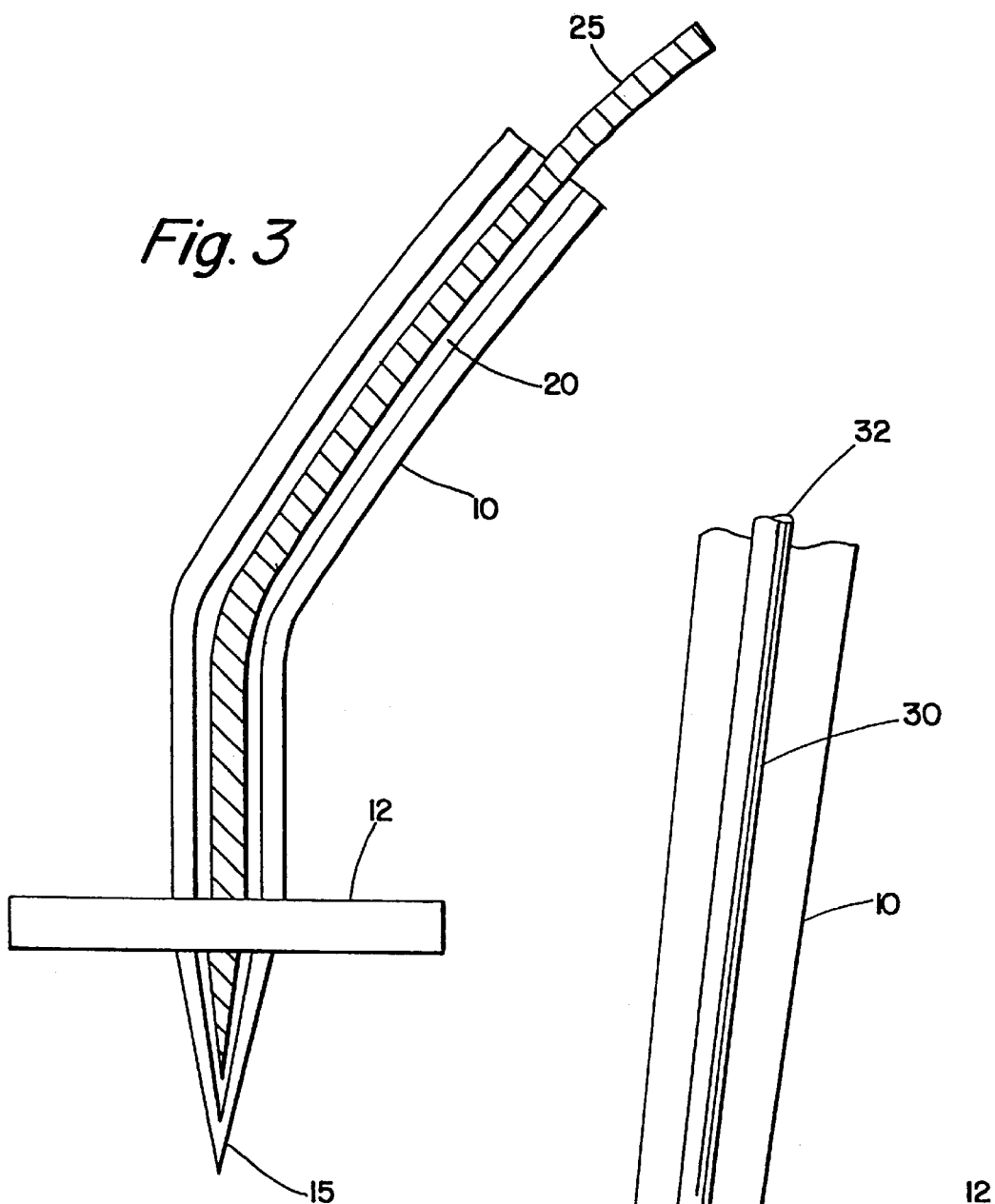

SUTURELESS VESSEL PLUG AND METHODS OF USE

This is a continuation of U.S. Application Ser. No. 09/199,233, filed Nov. 24, 1998 now U.S. Pat. No. 6,080,183, which is hereby expressly and fully incorporated herein by reference.

FIELD OF THE INVENTION

The present invention relates generally to a vessel plug which provides occlusion to an opening in a blood vessel. Sutures may be placed on the blood vessel around the plug. Alternatively, the opening in the vessel may be occluded without sutures.

BACKGROUND OF THE INVENTION

Blood vessels, either veins or arteries, are often punctured or incised to allow insertion of a cannula, catheter, or endovascular instruments during surgical or interventional procedures. For example, during open-heart coronary bypass grafting surgeries, venous return cannulas are often inserted in the superior vena cava, inferior vena cava, or the right atrium, whereas an arterial cannula is inserted in the femoral artery to complete cardiopulmonary bypass. During minimally invasive cardiac surgeries, various endoscopic instruments and cannulas are inserted in a patient's ascending aorta through the chest wall to establish cardiopulmonary bypass and cardioplegia. After removal of these medical devices, the blood vessel is often left with an open wound. Sutures are generally required around the opening due to the large diameter of these medical devices.

The most common technique for quickly occluding vessel holes is the finger of an operator, who can quickly and easily locate the source of the leakage and occlude it with the tip of his or her finger. Disadvantages to this method are that (1) one hand of the operator is occupied holding the blood vessel, (2) having the operator's hand around the vessel opening reduces space available for suturing the blood vessel, and (3) vessel visualization and vessel access are compromised around the vessel opening due to crowding from the operator's hand and arm.

Another common method of occluding an opening on a blood vessel employs a mechanical clamp (partial occlusion clamp). A clamp, when positioned and closed over an opening of a vessel, can isolate the vessel hole from blood flow. Disadvantages associated with this method are that (1) not all vessels have sufficient space around the opening to position a clamp, (2) a blood vessel may be damaged from clamping its wall, and (3) a diseased blood vessel may shower emboli, and /or may be dissected, creating a false lumen.

A need exists for space conserving devices that provide sutureless occlusion of an opening of a blood vessel and provide minimum vessel manipulation and deformation during use.

SUMMARY OF THE INVENTION

The present invention provides a sutureless vessel plug for maintaining hemostasis of a blood vessel having an open wound. The plug may be used to occlude cavities other than vessels, such as abdominal fistula and the like. Moreover, the plug may be constructed of materials suitable for permanent implantation.

In one embodiment, the vessel plug includes a handle having a proximal end and a distal end. A flange is attached to the distal end of the handle. A tip, which extends distally beyond the flange, is shaped to engage the vessel opening to block blood flow. In certain embodiments, the handle may include a lumen that is closed at the distal end. A preformed mandrel, adapted for insertion into the lumen of the handle, may be used to adjust the angle of the tip relative to the handle, so that the contour of the plug and the tip may be manipulated to provide optimal insertion into the vessel or cavities.

In another embodiment, the plug may include a tip that is deformable to engage an interior of a vessel. Certain tip embodiments allow the deformation to be actuated by struts and a spring, an inflatable member, or a phase transition within a shape memory material. The tip may further operate to expand radially outward to engage the interior wall of a vessel.

In other embodiments, the flange is rectangular, oval, H-shaped, star shaped, ratchet shaped, or other geometric shapes. The flange allows the plug to be sutured onto the vessel or allows sutures be placed around the vessel opening. The flange may be flat, curved, tapered, or ridged to conform to the surface of a vessel. In another embodiment, the flange may be made of both stiff and soft material, optionally with adhesive on one surface to engage the wall of the vessel. Certain flange embodiments may include a plurality of suction ports, which operate to engage the vessel wall by vacuum, the ports communicating with a vacuum tube carried by the handle. During use, this flange is tightly bound to the vessel wall under negative pressure, thereby negating the need for sutures.

The methods of the present invention include maintaining hemostasis of a blood vessel having an opening using the sutureless vessel plug as described above. After an open wound on a blood vessel, such as an aorta, carotid artery, or vein, is located, the tip of the plug is inserted into the vessel opening, so that the flange engages the wall of the vessel, thereby blocking the flow of blood through the opening. The plug may be preformed and restrained prior to introduction via an introducer sheath. In embodiments that include a preformed mandrel, the methods further include the step of inserting the mandrel into a lumen of the handle to adjust the angle of the tip relative to the handle during insertion of the plug into the vessel opening.

It will be understood that there are several advantages in using the vessel plug as disclosed herein. For example, (1) the plug does not require suturing and may be self attaching or held in place; (2) the plug may be introduced remotely or directly onto a vessel; (3) the plug is space conserving; (4) vessel manipulation and deformation is minimized, thereby reducing risk of vessel damage and emboli generation; (5) the plug provides open access to the vessel near the insertion site; (6) the plug can be used in minimally invasive surgical procedures; and (7) the plug may be used to occlude body cavities other than vessels.

BRIEF DESCRIPTION OF DRAWINGS

FIG. 1 depicts a preferred embodiment of a vessel plug in an opening of a blood vessel according to the present invention.

FIG. 3 depicts another embodiment of a vessel plug carrying a mandrel in a lumen of its handle.

FIG. 4 depicts another embodiment of a vessel plug having vacuum ports in its flange.

DETAILED DESCRIPTION

The devices and methods of the invention facilitate hemostasis of punctured or incised blood vessels by providing a sutureless vessel plug. In addition, the invention facilitates hemostasis in both minimally invasive surgical techniques, such as port access, and emboli management, the combination of which is being developed as a new field in surgical innovation.

Referring more to the drawings, FIG. 1 depicts a preferred embodiment of a vessel plug according to the present invention. The plug has handle 10, flange 12, and tapered tip 15. In use, tip 15 is inserted into an opening in vessel wall 1. Flange 12 engages the vessel wall and controls the depth of the tip's insertion into the vessel wall. Handle 15 is used to position the tip and/or to attach to other devices, such as tubing or lights. The vessel wall opening is occluded by a combination of vessel stretching and pressure generated against the wall by the flange, thereby blocking blood flow through the vessel wall opening, achieving hemostasis.

Figure 2A:
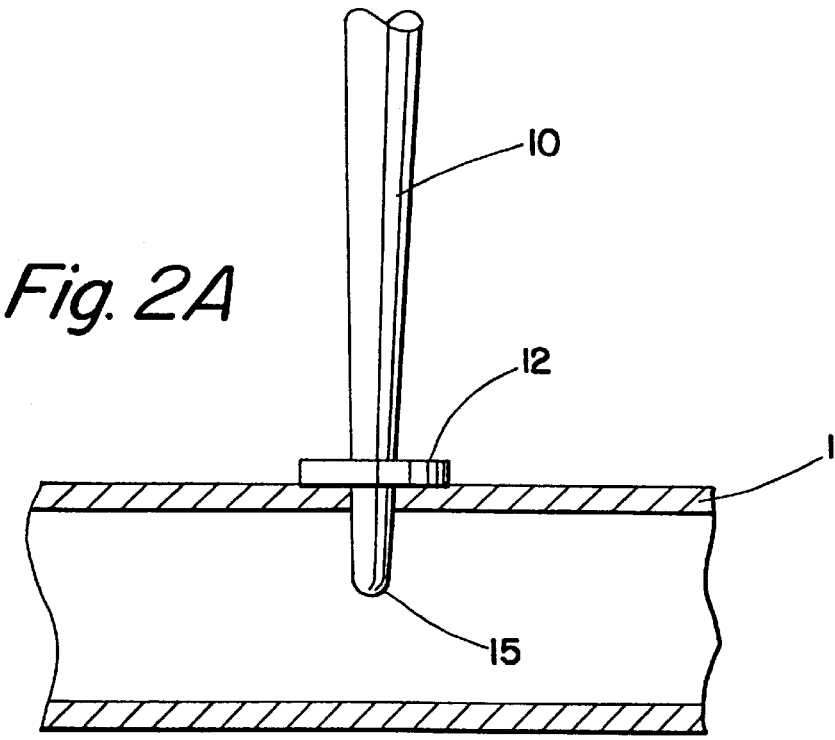
FIG. 2A depicts an alternative embodiment of a vessel plug having a deformable tip inserted through a vessel opening according to the present invention.
Figure 2B:
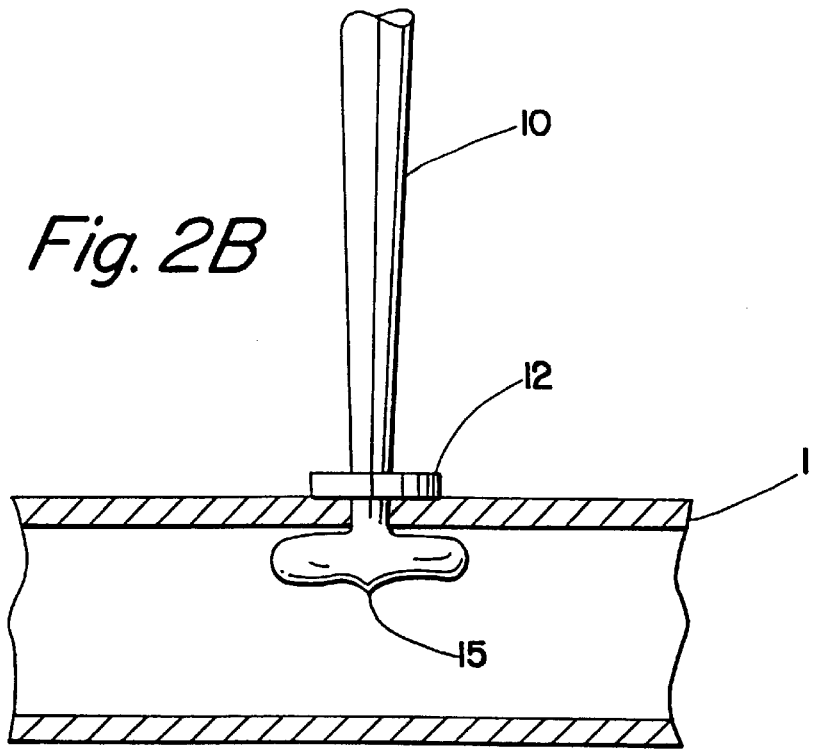
FIG. 2B depicts the alternative embodiment of a vessel plug in FIG. 2A having the tip deformed to seal the vessel opening.
Figure 2C:
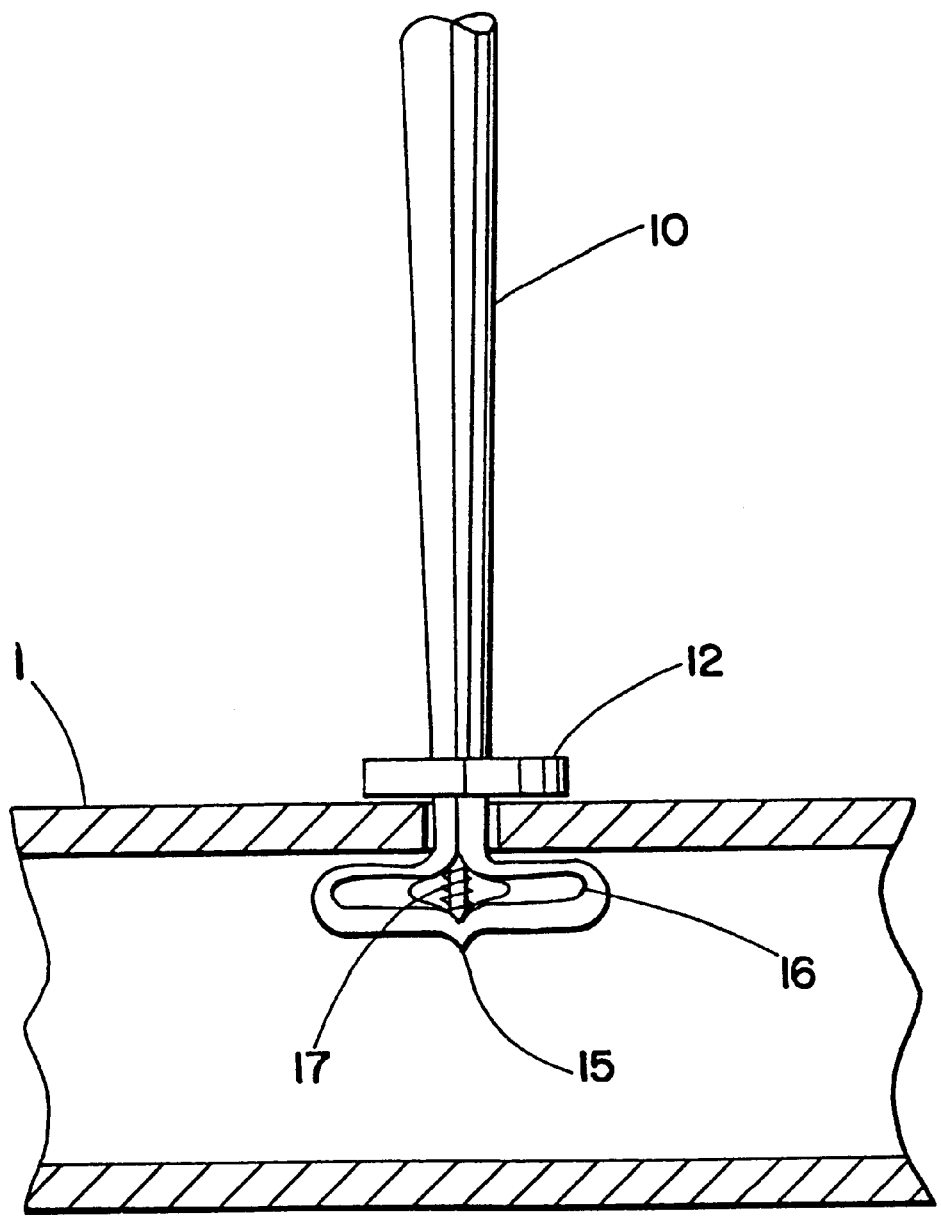
FIG. 2C depicts the alternative embodiment of a vessel plug in FIG. 2A having a deformable tip with struts.
Figure 5A:
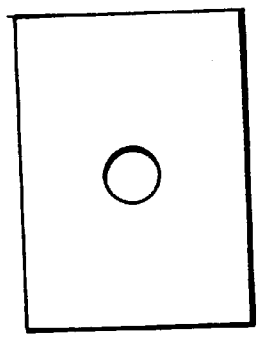
FIG. 5A depicts a top view of a flange embodiment having a rectangular shape.
Figure 5B:
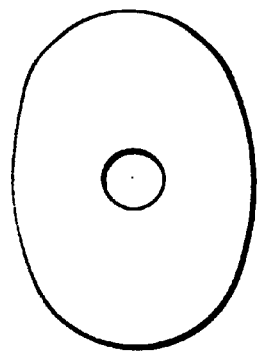
FIG. 5B depicts a top view of a flange embodiment having an oval shape.
Figure 5C:
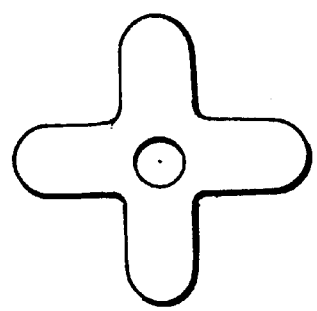
FIG. 5C depicts a top view of a flange embodiment having a star shape.
Figure 5D:
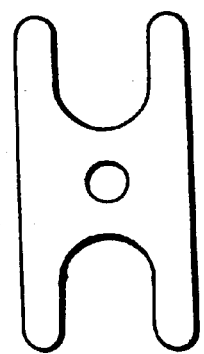
FIG. 5D depicts a top view of a flange embodiment having an H shape.
Figure 5E:
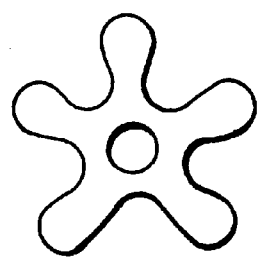
FIG. 5E depicts a top view of a flange embodiment having a petal shape.
Figure 5F:
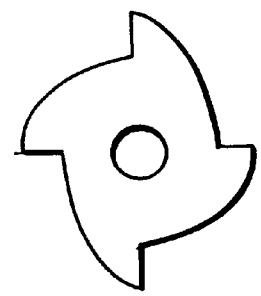
FIG. 5F depicts a top view of a flange embodiment having a ratchet shape.

Alternative embodiments of the vessel plug comprising an actuated tip are depicted in FIG. 2. In FIG. 2A, tip 15 is inserted into vessel opening. In FIG. 2B and FIG. 2C, the indwelling portion of the plug deforms inside the vessel and engages the interior surface of the vessel, thereby sealing fluid or blood flow through the vessel opening. The deformation may be actuated using mechanical struts and springs 17, inflatable members, and/or self-inflatable deforming shape memory materials.

FIG. 3 depicts another embodiment of the vessel plug that includes lumen 20 in handle 10. The lumen is closed at tip 15. Mandrel 25 is inserted into lumen 20 of the handle so that the handle and the tip can be adjusted to an optimal angle for easier insertion into an opening of a vessel. The handle and the tip may be constructed of flexible material to allow manipulation by the mandrel.

FIG. 4 depicts another embodiment of the vessel plug having suction ports 35 in its flange. Flange 12 may include 1, 2, 3, 4, 5, 6 or more suction ports, each of which communicate with suction lumen 30 in handle 10. Proximal end 32 of the suction lumen is adapted for attachment to a vacuum. In use, the vessel plug is inserted into an opening of a vessel, so that flange 12 engages the vessel wall. Proximal end 32 is connected to a vacuum, and the vessel wall opening is sealed from blood flow. Furthermore, the suction ports may be used to facilitate removal of unwanted fluid, blood, or air from the surgical field. In addition, certain embodiments may include suction ports in the non-dwelling portion of the cannula. The suction ports on the flange and the non-indwelling portion of the cannula may be used to stabilize the plug in position.

The flange may be constructed of different geometric shapes, such as rectangular, oval, star, H-shaped, petal, or ratchet, as depicted in FIG. 5A through 5F. The flange provides a depth gage for insertion of the plug into a vessel. The different geometric shapes of the flange facilitate suturing and/or vessel manipulation around the vessel wall.

Figure 6A:
FIG. 6A depicts a side view of a flange embodiment having a straight profile.
Figure 6B:
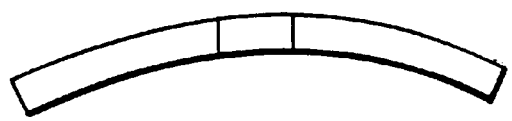
FIG. 6B depicts a side view of a flange embodiment having a curved profile.
Figure 6C:
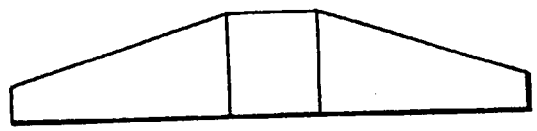
FIG. 6C depicts a side view of a flange embodiment having a tapered profile.
Figure 6D:
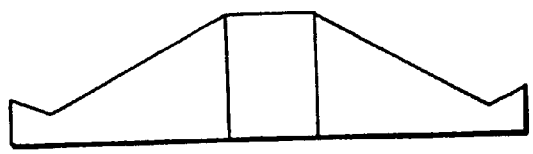
FIG. 6D depicts a side view of a flange embodiment having a complex tapered profile.
Figure 6E:
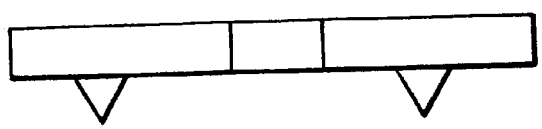
FIG. 6E depicts a side view of a flange embodiment having a ridged profile.
Figure 6F:
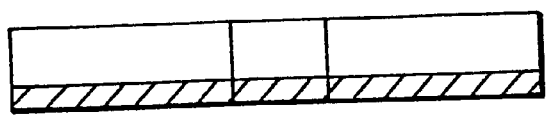
FIG. 6F depicts a side view of a flange embodiment having a multiple profile.

The flange may take on different profiles, when viewed from its side, as depicted in FIG. 6A through 6F. In FIG. 6B, the curved construction of a flange approximates the contour of a blood vessel, thereby providing better contact between the flange and the vessel wall. In FIG. 6C and 6D, the tapered and complex tapered profiles allow the plug to be constructed with added stability between the flange and the vessel wall during insertion. In FIG. 6E, the ridged construction of a flange provides a better grip of the plug on the blood vessel during its insertion. In FIG. 6F, the flange is constructed of a stiff top layer and a soft bottom layer. The soft bottom layer allows better contact between the flange and the outer vessel wall. This multiple profiled construction also allows adhesive material to be placed onto the soft bottom layer for self-occlusion of a vessel opening.

The length of a tip will generally be between 0.2 and 3 centimeters, preferably approximately 0.5 to 1 centimeter. The width of a flange will generally be between 0.5 and 3 centimeters, preferably approximately 1 centimeter. The length of a handle will generally be between 5 and 25 centimeters, preferably approximately 10 centimeters. The outer diameter of a handle at its proximal end will generally be between 0.2 and 1.5 centimeters, preferably approximately 0.5 to 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claims.

What is claimed is:

1. A vessel plug for maintaining hemostasis of a vessel having an opening, comprising:

a handle having a proximal end, a distal end, and a lumen which is closed at the distal end;

a preformed mandrel inserted into the lumen of the handle to adjust the angle of the tip relative the handle;

a flange attached to the distal end of the handle; and a tip that extends distally beyond the flange, the tip shaped to engage the opening in the vessel to block the flow of blood through the opening.

2. The vessel plug of claim 1, wherein the flange is rectangular.

3. The vessel plug of claim 1, wherein the flange is H-shaped.

4. The vessel plug of claim 1, wherein the tip is deformable to engage an interior wall of the vessel.

5. The vessel plug of claim 1, wherein the tip operates to expand radially outward to engage an interior wall of the vessel.

6. The vessel plug of claim 1, wherein the flange has a curved profile to conform to the surface of a vessel.

7. The vessel plug of claim 4, wherein the deformation is actuated by struts and a spring.

8. The vessel plug of claim 4, wherein the deformation is actuated by an inflatable member.

9. The vessel plug of claim 4, wherein the deformation is actuated by a phase transition within shape memory material.

10. The vessel plug of claim 1, wherein the flange includes a plurality of suction ports that operate to engage the vessel wall by vacuum.

11. The vessel plug of claim 10, wherein the handle carries a vacuum tube which communicates with the suction ports.

12. The vessel plug of claim 1, wherein the flange further comprises an adhesive on the surface which engages the wall of the vessel.

13. A method for maintaining hemostasis of extravasate from an aorta having an opening from the exterior wall of the aorta to the aortic lumen, comprising the steps of:

providing a vessel plug comprising a handle, a flange attached to a distal end of the handle, and a tip which extends distally beyond the flange; and inserting the tip into the opening on the exterior wall of the aorta until the flange engages the exterior wall of the aorta, thereby blocking the flow of blood from the aorta through the opening.

14. The method of claim 13, further comprising the step of suturing the aorta adjacent the flange.

15. The method of claim 13, further comprising the step of inserting a preformed mandrel into the handle to adjust the angle of the tip relative the handle.

* * * * *